(12) United States Patent
Ishihara et al.

(10) Patent No.: US 6,214,893 B1
(45) Date of Patent: Apr. 10, 2001

(54) POLYESTER DECOMPOSITION PROCESS AND POLYESTER MONOMERIZATION SYSTEM

(75) Inventors: Nobuo Ishihara; Wataru Kawamura; Masahiro Kishi; Kikuo Okazaki, all of Takasago (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 09/341,591

(22) PCT Filed: Nov. 13, 1998

(86) PCT No.: PCT/JP98/05102

§ 371 Date: Jul. 13, 1999

§ 102(e) Date: Jul. 13, 1999

(30) Foreign Application Priority Data

Nov. 14, 1997 (JP) .................................................. 9-313082

(51) Int. Cl.$^7$ ........................................... C08J 11/04
(52) U.S. Cl. ............................................. 521/48; 521/48.5
(58) Field of Search ....................................... 521/48, 48.5

(56) References Cited

U.S. PATENT DOCUMENTS

| | | | |
|---|---|---|---|
| 3,907,868 | * 9/1975 | Currie et al. | 260/475 D |
| 4,609,680 | 9/1986 | Fujita et al. | 521/48 |
| 4,876,378 | * 10/1989 | Van Sickle | 560/78 |
| 5,576,456 | * 11/1996 | Gamble et al. | 560/78 |
| 5,747,547 | * 5/1998 | Naujokas et al. | 521/48.5 |

FOREIGN PATENT DOCUMENTS

| | | | |
|---|---|---|---|
| 0758640 A1 | 2/1997 | (EP) | C07C/67/03 |
| 60-248646 | 12/1985 | (JP) | C07C/69/82 |
| 9-118639 | 5/1997 | (JP) | C07C/27/26 |

* cited by examiner

Primary Examiner—Edward J. Cain
Assistant Examiner—Katarzyna Wyrozebski-Lee
(74) Attorney, Agent, or Firm—Myers Bigel Sibley & Sajovec, P.A.

(57) ABSTRACT

The present invention provides a process for the decomposition of a polyester which can accelerate the reaction for decomposing the polyester to form monomers serving as raw materials or raw material derivatives. This process for the decomposition of a polyester is characterized in that the polyester is decomposed by solvolysis with methanol to form a dimethyl carboxylate and a dihydroxy compound, and these decomposition products are added to and mixed with a melt of the polyester for the purpose of decomposing the polyester by solvolysis.

9 Claims, 2 Drawing Sheets

POLYESTER DECOMPOSITION PROCESS AND POLYESTER MONOMERIZATION SYSTEM

TECHNICAL FIELD

This invention relates to a process for the decomposition of a polyester which can accelerate the reaction for decomposing the polyester to form monomers serving as raw materials or raw material derivatives, and a system for the monomerization of a polyester.

BACKGROUND ART

The methods for reusing a polyester as the same type of polyester material include a material cycle and a chemical cycle. In the material cycle, a polyester is softened, for example, by the application of heat and then re-formed. This method of reuse is simple in process construction and involves low recycling costs per cycle. However, since the properties (e.g., moldability) of the original material are deteriorated as the re-forming is repeated, the number of recycles is limited. Moreover, the material must inevitably be changed over to applications having lower property requirements.

On the other hand, the chemical cycle comprises returning a polyester to the form of raw materials, purifying them, and synthesizing a polyester again. Consequently, this method requires a complicated system and involve high recycling costs per cycle. However, it can provide much value added because the number of recycles is markedly increased and the application of the recycled material is not limited.

DISCLOSURE OF THE INVENTION

Although a large number of processes for the monomerization of polyesters are known, a satisfactorily high reaction rate cannot be achieved because they are based on a surface reaction. Typical processes include solvolysis with methanol and hydrolysis with water. However, since polyesters are insoluble in methanol or water, the reaction is carried out in a system having two separated phases. Accordingly, none of them has been satisfactory from the viewpoint of reaction conditions such as reaction time and temperature.

For example, it has been reported by Sako et al. in the Institute for Material Science, the Agency of Industrial Science and Technology that the decomposition of PET in methanol requires treatment at 300° C. and 80 atmospheres for 30 minutes. However, the present inventors have confirmed that the decomposition rate of PET depends on its specific surface area. Specifically, when a test was carried out by grinding an equal weight of PET finely and dividing the reaction vessel so as not to cause the PET to agglomerate again during melting, the PET could be completely decomposed in a period of 10 to 20 minutes. Thus, it would be desirable to provide a simple method which permits the effective specific surface area for reaction to be increased in actual plants.

According to the present invention, in the decomposition of a polyester, the decomposition products obtained by solvolysis, together with the polyester, are added to the reaction system. For example, in the decomposition of a polyester, the dimethyl carboxylate and dihydroxy compound corresponding to the decomposition products obtained by solvolysis with methanol, together with the polyester, are added to the reaction system. Thus, the decomposition rate can be enhanced. The reason for this is considered to be that the aforesaid dimethyl carboxylate corresponding to a decomposition product dissolves the polyester at temperatures higher than its melting point to increase the effective area for reaction or to aid in the dissolution of the polyester in methanol or its mixing with methanol.

That is, the present invention provides a process for the decomposition of a polyester which comprises decomposing the polyester by solvolysis to form monomers, wherein the decomposition products obtained by solvolysis are recycled as solvents for the polyester. For example, according to a preferred embodiment of the present invention, a polyester is decomposed by solvolysis with methanol to form a dimethyl carboxylate and a dihydroxy compound, and these decomposition products are previously added to and mixed with a melt of the polyester for the purpose of decomposing the polyester by solvolysis.

The solvent used in the aforesaid solvolysis generally comprises a polar solvent. Alcohols are preferred, lower alkyl alcohols (commonly alkyl alcohols having 1 to 5 carbon atoms) are more preferred, and methanol is most preferred.

As described above, the present invention is characterized in that the decomposition products are recycled as solvents for the polyester. When a lower alkyl alcohol is used as the polar solvent, the decomposition products being recycled are a dialkyl carboxylate and a dihydroxy compound. When methanol is used as the polar solvent, the decomposition products being recycled are a dimethyl carboxylate and a dihydroxy compound.

The polyesters which can be monomerized or decomposed according to the present invention include, for example, polyethylene-butylene terephthalate (PEBT), polyethylene terephthalate (PET), polybutylene terephthalate (PBT), polycyclohexanedimethylene terephthalate (PCT), polyethylene naphthalate (PEN), polybutylene naphthalate (PBN) and polycarbonate (PC).

In the examples which will be given later, the effectiveness of the present invention was confirmed for all of the polyesters tested. Accordingly, it is believed that the process of the present invention is universally useful for polyesters.

In the practice of the present invention, it is preferable to recover the aforesaid decomposition products with progressive reduction in pressure and recycle them.

Moreover, the present invention also provides a system for the monomerization of a polyester which comprises a high-pressure reaction vessel for receiving a molten polyester and reacting it with a solvent, pressure reducing means and recovery means for progressively reducing the pressure of the decomposition products formed in the high-pressure reaction vessel and thereby recovering the decomposition products, and lines for recycling the decomposition products from the recovery means to the high-pressure reaction vessel as solvents for the polyester. It is to be understood that an insufficiently decomposed oligomer and/or the solvent may also be recycled.

It may be expected that this monomerization system can achieve high recoveries in a short period of time. Generally, recovery tanks are used as the aforesaid recovery means.

As is evident from the above description, the present invention provides a process for the decomposition of a polyester wherein the decomposition products obtained by the solvolytic decomposition of a polyester, together with the polyester, are added to the reaction system, so that its monomerization can be achieved under satisfactory reaction conditions such as reaction time and temperature.

Moreover, the present invention also provides a process for the decomposition of a polyester and a system for the monomerization of a polyester, wherein the aforesaid decomposition products are recovered with progressive reduction in pressure and recycled, so that high recoveries can be achieved in a short period of time.

BEST MODE FOR CARRYING OUT THE INVENTION

Figure 1:
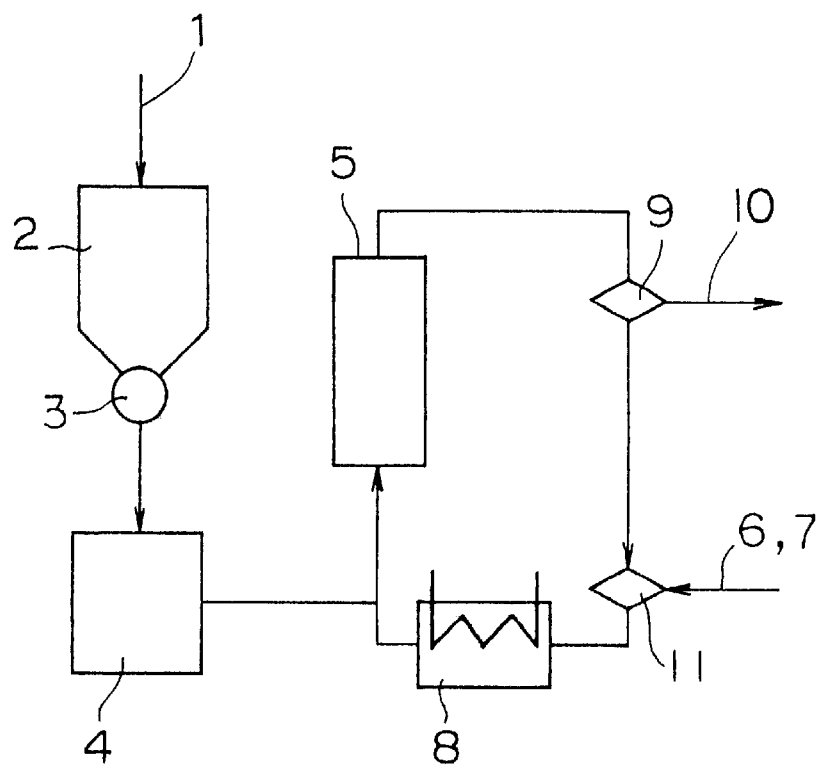
FIG. 1 is a flow diagram illustrating a process in accordance with one embodiment of the present invention.

Several embodiments of the present invention are described below. These embodiments are intended to illustrate the conception of the present invention in a concrete form, and are not to be construed to limit the technical scope of the present invention.
First embodiment FIG. 1 illustrates a polyester decomposition process in accordance with one embodiment of the present invention. In FIG. 1, a polyester 1 is passed through a hopper 2 and a feeder 3, melted in a melter 4, and fed to a reactor 5. On the other hand, methanol and a catalyst 6 are added to part of the decomposition products 7. The resulting mixture is heated in a heater 8, fed to reactor 5, and used therein for solvolysis. Part 10 of the decomposition products so formed are recovered at a branch point 9 on the product discharge side. As described above, the remainder is mixed with methanol and catalyst 6, and recycled to reactor 5. Numeral 11 designates a branch point on the methanol injection side.

The amount of the decomposition products recycled as described above is preferably in the range of 30 to 500 parts by weight per 100 parts by weight of the polyester.

That is, this embodiment provides a treating process in which part of the decomposition products are recycled to reactor 5, instead of separating all of the decomposition products. According to this treating process, the dimethyl carboxylate and dihydroxy compound corresponding to the decomposition products can readily by introduced into reactor 5 and thermal losses can be minimized.

Figure 3:
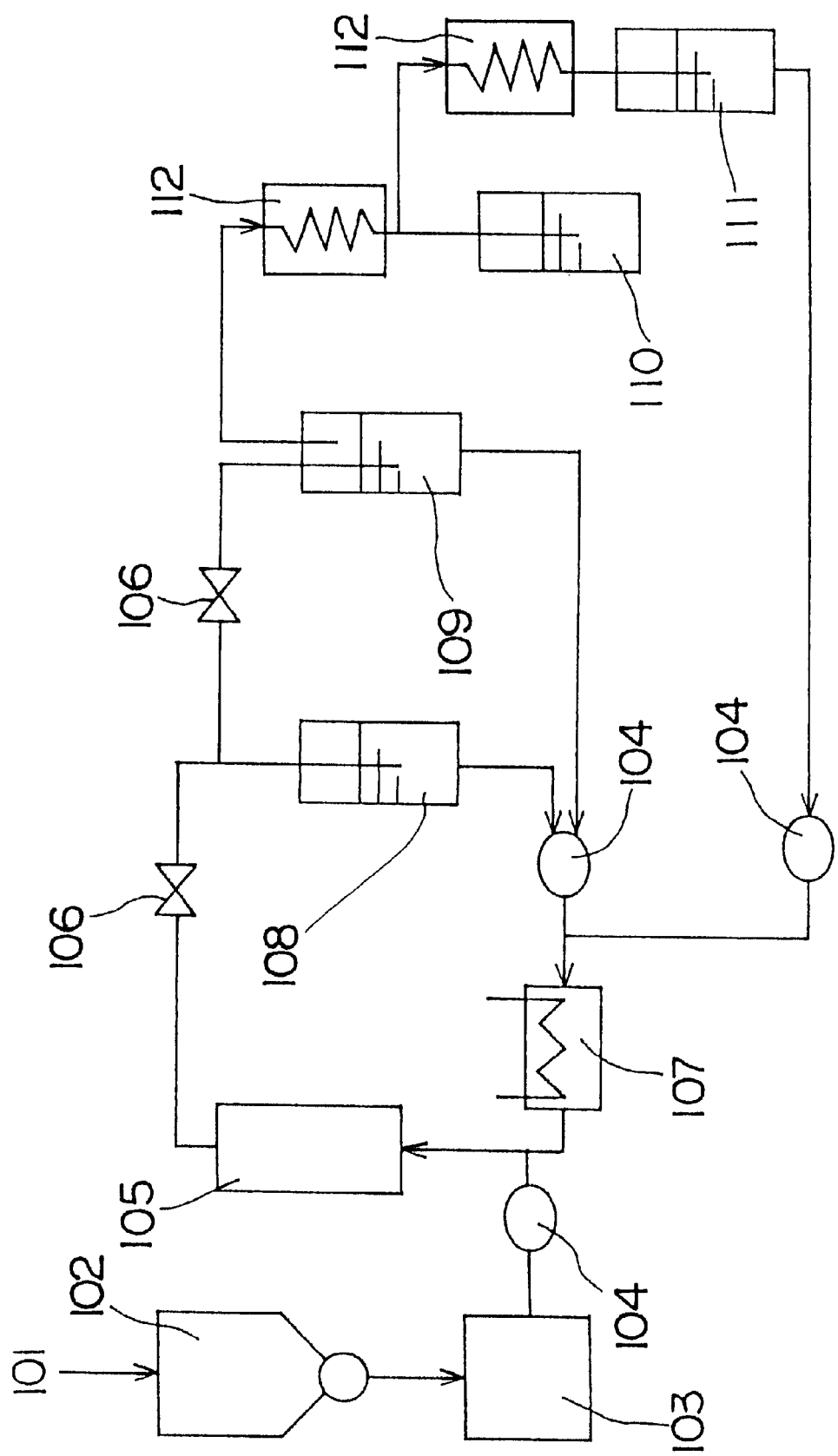
FIG. 3 is a flow diagram illustrating a process in accordance with another embodiment of the present invention.

Thus, in order to achieve the desired effects, the process of this embodiment comprises feeding a molten polyester to a reactor, feeding a heated mixture of methanol and a catalyst to the reactor, decomposing the aforesaid polyester by solvolysis with methanol, and recycling part of the dimethyl carboxylate and dihydroxy compound obtained as decomposition products to the aforesaid reactor for the purpose of decomposing the polyester by solvolysis.
Second embodiment A process using a monomerization system in accordance with another embodiment of the present invention is illustrated in FIG. 3.

In this process, a polyester comprising PET 101 is thrown into a hopper 102, and then fed to a high-pressure reaction vessel 105 through a melter 103 by means of a pressure pump 104. Thus, the PET is decomposed to monomers by solvolysis with methanol fed through another line. The decomposition products are passed through a pressure reducing valve 106 and thereby reduced in pressure. As a result of pressure reduction to 2–10 atmospheres, an insufficiently decomposed oligomer condenses in a crude oligomer tank 108. Further pressure reduction of the gaseous components causes dimethyl terephthalate (DMT) to condense in a crude DMT tank 109. When the temperature of the remaining gas is reduced to 80° C. with a condenser 112, ethylene glycol (EG) condenses in a crude EG tank 110. Finally, further cooling to room temperature with another condenser 112, the remaining methanol condenses in a crude methanol tank 111. Similarly to the above-described first embodiment, the aforesaid oligomer, DMT, EG and methanol are partly recycled through pressure pumps 104 and a heater 107.

As described above, the polyester monomerization system in accordance with this embodiment is equipped with lines through which the decomposition products formed in a high-pressure reaction vessel are progressively reduced in pressure by pressure reducing means, recovered by a plurality of recovery means, and then recycled from the plurality of recovery means to the aforesaid high-pressure reaction vessel as solvents for the polyester. Moreover, as explained in connection with this embodiment, not only the decomposition products, but also an insufficiently decomposed oligomer and/or the solvent (e.g., methanol) may be recycled. It may be expected that this system can achieve high recoveries in a short period of time.

EXAMPLE 1

This Example 1 is an example corresponding to the first embodiment described above with reference to FIG. 1.

Figure 2:
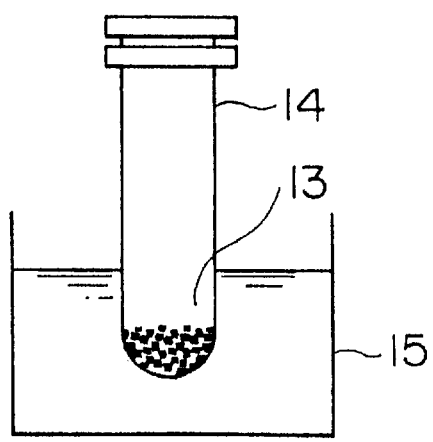
FIG. 2 is a schematic view showing the monomerization method employed in Example 1.

In this example, an autoclave as shown in FIG. 2 was used as reactor 5 shown in FIG. 1.

A reaction mixture 13 composed of a polyester, a catalyst, methanol, a dimethyl carboxylate and a dihydroxy compound was placed in an autoclave 14, which was tightly sealed and purged with nitrogen. Then, this autoclave 14 was heated in a tin bath 15. The case in which the corresponding dimethyl carboxylate and the corresponding dihydroxy compound, together with the polyester, were added to the autoclave in twice the molar amounts produced when the polyester was completely decomposed by solvolysis was compared with the case in which neither the corresponding dimethyl carboxylate nor the corresponding dihydroxy compound was added. In each case, experiments were performed at two different reaction temperatures. When the reaction temperature was in the subcritical region of methanol, zinc acetate was added as a catalyst. When the reaction temperature was in the supercritical region of methanol, no catalyst was added and the pressure was controlled.

A total of six polyesters were tested in the above-described manner. The results thus obtained are shown in Table 1. The details of the conditions and the results are described below.

The degree of decomposition was calculated by regarding the methanol-insoluble solid remaining after the reaction as undecomposed matter. When the degree of decomposition was greater than 95%, the products were analyzed by gas chromatography, liquid chromatography or mass spectrometry. Thus, it was confirmed that the polyester was decomposed to the corresponding dimethyl carboxylate and dihydroxy compound, and the content of impurities was less than 10% of the peak detected in each analysis.

TABLE 1

| No., Reactant | Dimethyl carboxylate | Dihydroxy compound | Catalyst | Methanol | Reaction temperature (K.) | Reaction time (min) | Pressure (Mpa) | Degree of decomposition (%) |
|---|---|---|---|---|---|---|---|---|
| 1 | PET | DMT | EG | Zn(Oac)2 | | | | Vaper |
| 1-1 | 192 mg | 388 mg | 124 mg | 1 mg | 600 mg | 493 | 120 | pressure | >95% |
| 1-2 | ↑ | 0 mg | 0 mg | ↑ | ↑ | ↑ | ↑ | ↑ | 65% |
| 1-3 | 192 mg | 388 mg | 124 mg | 0 mg | 600 mg | 573 | 15 | 10 | >95% |
| 1-4 | ↑ | 0 mg | 0 mg | ↑ | ↑ | ↑ | ↑ | ↑ | 70% |
| 2 | PBT | DMT | TMG | Zn(Oac)2 | | | | | Vaper |
| 2-1 | 220 mg | 388 mg | 180 mg | 1 mg | 600 mg | 493 | 90 | pressure | >95% |
| 2-2 | ↑ | 0 mg | 0 mg | ↑ | ↑ | ↑ | ↑ | ↑ | 75% |
| 2-3 | 220 mg | 388 mg | 180 mg | 0 mg | 600 mg | 573 | 12 | 10 | >95% |
| 2-4 | ↑ | 0 mg | 0 mg | ↑ | ↑ | ↑ | ↑ | ↑ | 70 |
| 3 | PCT | DMT | CHDM | Zn(Oac)2 | | | | | Vaper |
| 3-1 | 272 mg | 388 mg | 284 mg | 1 mg | 600 mg | 493 | 180 | pressure | >95% |
| 3-2 | ↑ | 0 mg | 0 mg | ↑ | ↑ | ↑ | ↑ | ↑ | 80% |
| 3-3 | 272 mg | 388 mg | 284 mg | 0 mg | 600 mg | 623 | 20 | 12 | >95% |
| 3-4 | ↑ | 0 mg | 0 mg | ↑ | ↑ | ↑ | ↑ | ↑ | 85% |
| 4 | PEN | NDCM | EG | Zn(Oac)2 | | | | | Vaper |
| 4-1 | 242 mg | 488 mg | 124 mg | 1 mg | 600 mg | 493 | 150 | pressure | >95% |
| 4-2 | ↑ | 0 mg | 0 mg | ↑ | ↑ | ↑ | ↑ | ↑ | 75% |
| 4-3 | 242 mg | 488 mg | 124 mg | 0 mg | 600 mg | 623 | 15 | 12 | >95% |
| 4-4 | ↑ | 0 mg | 0 mg | ↑ | ↑ | ↑ | ↑ | ↑ | 75% |
| 5 | PBN | NDCM | TMG | Zn(Oac)2 | | | | | Vaper |
| 5-1 | 270 mg | 488 mg | 180 mg | 1 mg | 600 mg | 493 | 120 | pressure | >95% |
| 5-2 | ↑ | 0 mg | 0 mg | ↑ | ↑ | ↑ | ↑ | ↑ | 70% |
| 5-3 | 270 mg | 488 mg | 180 mg | 0 mg | 600 mg | 573 | 15 | 10 | >95% |
| 5-4 | ↑ | 0 mg | 0 mg | ↑ | ↑ | ↑ | ↑ | ↑ | 75% |
| 6 | PC | DMC | BPA | Zn(Oac)2 | | | | | Vaper |
| 6-1 | 254 mg | 180 mg | 456 mg | 1 mg | 600 mg | 493 | 50 | pressure | >95% |
| 6-2 | ↑ | 0 mg | 0 mg | ↑ | ↑ | ↑ | ↑ | ↑ | 80% |
| 6-3 | 254 mg | 180 mg | 456 mg | 0 mg | 600 mg | 573 | 10 | 10 | >95% |
| 6-4 | ↑ | 0 mg | 0 mg | ↑ | ↑ | ↑ | ↑ | ↑ | 90% |
| 7 | PC | DPC | BPA | Zn(Oac)2 | Phenol | | | | Vaper |
| 7-1 | 254 mg | 428 mg | 456 mg | 1 mg | 1800 mg | 493 | 50 | pressure | >95% |
| 7-2 | ↑ | 0 mg | 0 mg | ↑ | ↑ | ↑ | ↑ | ↑ | 80% |

(Note 1) Reactant
PET, polyethylene terephthalate; PBT, polybutylene terephthalate; PCT, polycyclohexanedimethylene terephthalate; PEN, polyethylene naphthalate; PBN, polybutylene naphthalate; PC, polycarbonate.
(Note 2) Dimethyl carboxylate
DMT, dimethyl terephthalate; NDCM, dimethyl 2,6-naphthalenedicarboxylate; DMC, dimethyl carbonate; DPC, diphenyl carbonate.
(Note 3) Dihydroxy compound
EG, ethylene glycol; TMG, tetramethylene glycol; CHDM, cyclohexanedimethanol; BPA, bisphenol A.
(Note 4) Solvent
$Zn(OAc)_2$: Zinc acetate.
The additives which are effective in the decomposition of each polyester are peculiar to the type of the polyester. Several examples of effective combinations are shown in Table 2.

TABLE 2

| Combination of additives | Effectively decomposable polyester |
|---|---|
| (1) DMT, EG | PET |
| (2) DMT, TMG | PBT |
| (3) DMT, CHDM | PCT |
| (4) NDCM, EG | PEN |
| (5) NDCM, TMG | PBN |
| (6) DMC, BPA | PC |
| (7) DPC, BPA | PC |

Thus, whether the polyester comprises any of polyethylene terephthalate (PET), polybutylene terephthalate (PBT), polycyclohexanedimethylene terephthalate (PCT), polyethylene naphthalate (PEN), polybutylene naphthalate (PBN) and polycarbonate (PC), and whether the reaction temperature is in the subcritical region or the supercritical region, the decomposition reaction could be accelerated, as shown in Table 1, by mixing the polyester with the two monomers obtained by solvolysis with methanol, prior to the start of the reaction.

EXAMPLE 2

A polyester monomerization system in accordance with the second embodiment of the present invention, which has been described above with reference to FIG. 3, was tested.

PET was thrown into hopper 102 and introduced into high-pressure reaction vessel 105. At this time, high-pressure reaction vessel 105 was controlled so as to have a temperature of 300° C. and a pressure of 10 MPa. After the PET was treated for a residence time of 10 minutes, the pressure of the decomposition products was reduced to 0.3 MPa. By maintaining the temperature of the system at about 240° C., an insufficiently decomposed oligomer was liquefied while DMT, EG and methanol remained in a gaseous state. Although the temperature was lower than the boiling point of DMT at this time, DMT was not liquefied because it coexisted with EG and methanol. This oligomer was allowed to react further and, at the same time, recycled at a solvent for PET. Moreover, DMT was made to condense by reducing the pressure to atmospheric pressure and maintaining the temperature at 200° C. Furthermore, EG and methanol were separated by repeated condensation. Part of the DMT and methanol were recycled as solvents and reagents. The recovered DMT, EG and methanol may be purified by distillation in later steps. Although the residence time in reaction vessel 105 was as short as 10 minutes, this process could produce an 85% yield of DMT and a 70% of EG.

The monomerization treatment of PET with methanol at 300° C. and 10 MPa generally requires a reaction time of 30 minutes or more. However, an oligomer, DMT and other products were successively recovered, recycled, and used as solvents for PET, a satisfactorily high reaction efficiency could be achieved in a reaction time of 10 minutes.

The whole contents of the specification, drawings, abstract and claims of Japanese Patent Application No. 313082/'97 are incorporated herein by reference.

The whole contents of the specification, drawings, abstract and claims of Japanese Patent Application No. 204339/'97 are incorporated herein by reference.

EXPLOITABILITY IN INDUSTRY

The present invention provides a process for the decomposition of a polyester wherein the decomposition products obtained by the solvolytic decomposition of a polyester, together with the polyester, are added to the reaction system, so that its monomerization can be achieved under satisfactory reaction conditions such as reaction time and temperature.

Moreover, the present invention also provides a process for the decomposition of a polyester and a system for the monomerization of a polyester, wherein the aforesaid decomposition products are recovered with progressive reduction in pressure and recycled, so that high recoveries can be achieved in a short period of time.

What is claimed is:

1. A process for the decomposition of a polyester which comprises decomposing the polyester by solvolysis to form monomers, wherein the decomposition products obtained by solvolysis are recycled as solvents for the polyester and the recycled decomposition products dissolve the polyester at temperatures higher than its melting point to enhance the decomposition rate of the polyester, wherein said process takes place at a temperature of from 493 K to 573 K.

2. A process for the decomposition of a polyester as claimed in claim 1 wherein the polyester is decomposed by solvolysis with an alcohol and the decomposition products obtained by solvolysis with the alcohol are recycled as solvents for the polyester.

3. A process for the decomposition of a polyester as claimed in claim 1 wherein the polyester is decomposed by solvolysis with a lower alkyl alcohol and the dialkyl carboxylate and dihydroxy compound obtained as decomposition products by solvolysis with the lower alkyl alcohol are recycled as solvents for the polyester.

4. A process for the decomposition of a polyester as claimed in claim 1 wherein the polyester is decomposed by solvolysis with methanol and the dimethyl carboxylate and dihydroxy compound obtained as decomposition products by solvolysis with methanol are recycled as solvents for the polyester.

5. A process for the decomposition of a polyester as claimed in claim 1 wherein the decomposition products are recovered with progressive reduction in pressure and recycled.

6. A process for the decomposition of a polyester as claimed in claim 1, wherein the polyester is decomposed by solvolysis with an alcohol and wherein a insufficiently decomposed oligomer is produced as a result of said step of decomposing the polyester, and wherein at least one of the insufficiently decomposed oligomer or alcohol is recycled as solvents for the polyester.

7. A process for the decomposition of a polyester as claimed in claim 6, wherein the alcohol is methanol.

8. A process for the decomposition of a polyester as claimed in claim 1, wherein the recycled decomposition products are present from 30 to 500 parts by weight per 100 parts by weight of the polyester.

9. A process for the decomposition of a polyester as claimed in claim 1, wherein the polyester is selected from the group consisting of polyethylene terephthalate, polybutylene terephthalate, polycyclohexanedimethylene terephthalate, polyethylene naphthalate, polybutylene naphthalate, and polycarbonate.

\* \* \* \* \*